US008552750B2

(12) United States Patent
Fougere

(10) Patent No.: US 8,552,750 B2
(45) Date of Patent: Oct. 8, 2013

(54) APPARATUS AND METHOD FOR THE MEASUREMENT OF ELECTRICAL CONDUCTIVITY AND DIELECTRIC CONSTANT OF HIGH IMPEDANCE FLUIDS

(75) Inventor: Alan J. Fougere, Falmouth, MA (US)

(73) Assignee: D-2, Inc., Pocasset, MA (US)

( * ) Notice: Subject to any disclaimer, the term of this patent is extended or adjusted under 35 U.S.C. 154(b) by 553 days.

(21) Appl. No.: 12/657,890

(22) Filed: Jan. 29, 2010

(65) Prior Publication Data
US 2010/0188111 A1   Jul. 29, 2010

Related U.S. Application Data

(60) Provisional application No. 61/206,289, filed on Jan. 29, 2009.

(51) Int. Cl.
   *G01R 27/08*   (2006.01)
(52) U.S. Cl.
   USPC .......................... 324/691; 324/639; 324/663
(58) Field of Classification Search
   USPC .................... 324/686–699, 442–470
   See application file for complete search history.

(56) References Cited

U.S. PATENT DOCUMENTS

| | | | | |
|---|---|---|---|---|
| 4,801,546 | A * | 1/1989 | Ackland | 435/287.1 |
| 5,334,940 | A * | 8/1994 | Blades | 324/442 |
| 6,664,793 | B1 * | 12/2003 | Sampson et al. | 324/439 |
| 6,741,084 | B2 * | 5/2004 | Pane et al. | 324/693 |
| 7,550,979 | B2 * | 6/2009 | Zhou et al. | 324/693 |
| 2007/0257679 | A1 * | 11/2007 | Fanini et al. | 324/366 |
| 2008/0079436 | A1 * | 4/2008 | Gollhardt et al. | 324/457 |

FOREIGN PATENT DOCUMENTS

JP           357079460       *  5/1982

* cited by examiner

*Primary Examiner* — Arleen M Vazquez
*Assistant Examiner* — Alesa Allgood
(74) *Attorney, Agent, or Firm* — Edwards Wildman Palmer LLP; Steven M. Jensen

(57) ABSTRACT

A sensor, a system of direct measurement using that sensor, and a method of direct and simultaneous measurement of conductivity and dielectric constant of a fluid, particularly high impedance, hydrocarbon-based fluids. The sensor has a cell that holds the fluids to be measured between a single pair of coaxial, bare metal electrodes connected through interface circuitry to measurement circuitry preferably implemented in one or several IC's. The sensor has a mutually compatible electrode geometry that provides both the correct cell constant for measurement of conductivity of hydrocarbons fluids (typical range 0-100,000 pS/cm), and a bulk capacitance (for use in dielectric constant measurement) in the range of measure of readily available low cost commercial IC's (having a typical capacitance measurement span of <10 pF, with a total bulk capacitance at the chip of <20 pF). The cell conductivity constant for use with hydrocarbon-based oils having a conductivity in the range of 1 to 500,000 pS/M is preferably less than or equal to about 0.1. The cell bulk capacitance with hydrocarbon fluids inside the sensor results in a bulk capacitance of at least about 4 pF. In one embodiment, the electronic circuitry is a Microcontroller/DSP that both generates synchronous drive signals at various frequencies, for both conductivity and dielectric constant measurements while directly digitizing and numerically processing the sensor output.

7 Claims, 4 Drawing Sheets

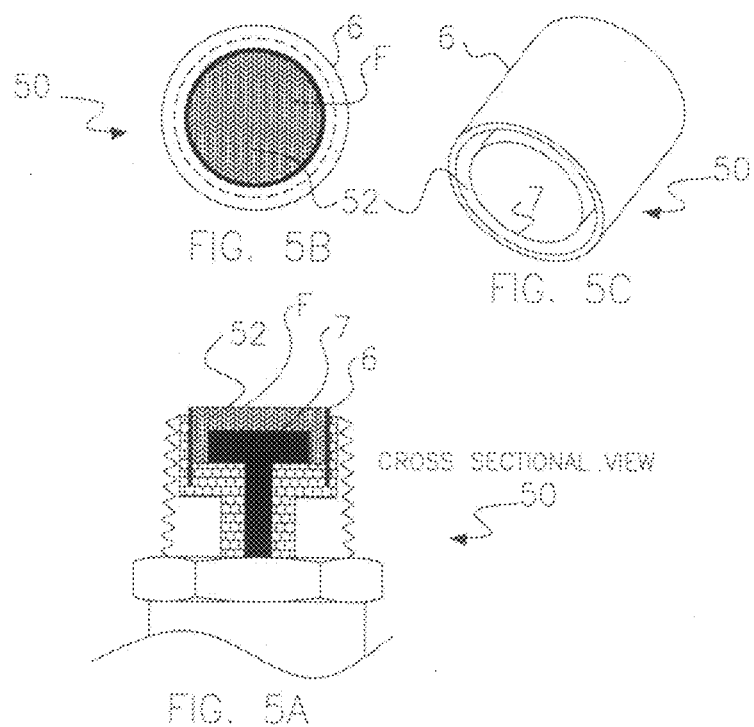
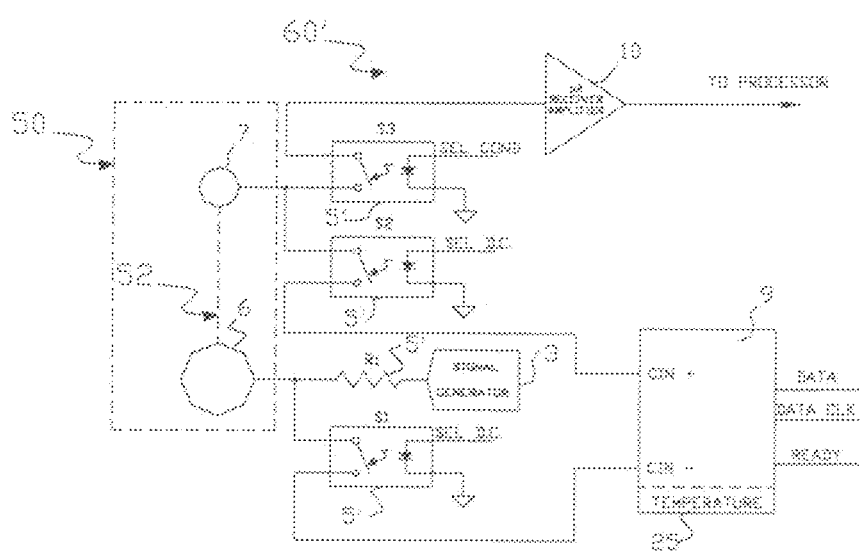

APPARATUS AND METHOD FOR THE MEASUREMENT OF ELECTRICAL CONDUCTIVITY AND DIELECTRIC CONSTANT OF HIGH IMPEDANCE FLUIDS

CROSS REFERENCE TO RELATED APPLICATIONS

This application claims priority under 35 USC 119(e) of U.S. Provisional Application No. 61/206,289 filed Jan. 29, 2009, the disclosure of which is incorporated herein by reference.

FIELD OF THE INVENTION

The present invention relates generally to the electrical measurement of physical parameters of fluids, and more particularly to the direct measurement of both the conductivity and dielectric constant of high impedance, hydrocarbon-based fluids, such as lubrication oils, kerosene (jet fuel), hydraulic fluids, and, solvents (e.g. isoparg). However, this invention also has applicability across the range to hydrocarbon fluid electrical conductivity measures, from 0 pS/m to 0.1 µS/cm.

BACKGROUND OF THE INVENTION

There is a long-standing need to monitor or inspect the condition of various hydrocarbon-based fluids such as aviation kerosene, lubricants and inks that are stored or flowing. Devices and techniques for the electrical measurement of parameters such as the conductivity, dielectric constant, and viscosity of fluids are known. Heretofore, most devices and techniques have used a sensor immersed in the fluid with electronic circuits to operate the sensor and produce the desired measurement. The physical properties of a sensor and the associated requirements of the electronic circuitry have typically restricted the direct measurement to that of only one parameter. In recent years, some techniques have been described that attempt to measure multiple parameters with one apparatus. For example, Visyx Technologies, Inc. has described a tuning fork resonator system driven at a spectrum of frequencies to generate data from which multiple fluid parameters are inferred by calculation. There is a need for a direct measurement of multiple fluid parameters that is not inferred by calculation. There is also a need for such direct measurements in real time, e.g. in the monitoring of fuel being fed to an engine as it is running.

There is also a long standing need to provide a device and system that measures both conductivity and dielectric constant, while simultaneously meeting other commercially important criteria such as: physical compactness, compatibility with low-cost, commercially-available electronics, cost-effective manufacturability, explosion resistance that meets recognized certification requirements, and commercially desirable levels of accuracy, resolution, stability and reliability in the measurements of the parameters of interest.

The invention should have the resolution to measure, for example, the level of water, absorbed or condensed as droplets, in a high impedance fluid such as lubricating oil, or, the ability to detect small quantities of drill mud contamination in hydraulic fluid.

D-2, Inc., the assignee of the present application, has previously developed methodologies for the measurement of electrical conductivity of aviation kerosene in a coaxial, two electrode sensor of the general type shown in FIG. 2, using circuitry of the general type shown in FIG. 3. D-2 has also adopted technologies using standard commercially available integrated circuits (IC's) to measure dielectric constant on a second pair of coaxial electrodes. These developments were effective for the measurement of aviation turbine fuel, but the complexity of a multiple electrode system does not lend itself to a low cost measurement of plural parameters of lubrication oil and like hydrocarbon-based fluids.

Low cost IC's that can measure conductivity or capacitance are known, e.g. for use with touch panels, but their operating characteristics such as their input capacitance range and capacitance off-setting capabilities are not suitable for use with this known hydrocarbon fuel sensor.

SUMMARY OF THE INVENTION

The present invention provides a sensor, system of measurement, and method of measurement of conductivity and dielectric constant of a fluid, particularly high impedance, hydrocarbon-based fluids, on a single pair of coaxial electrodes combined with unique sensor signal processors. This invention uses mutually compatible sensor geometry for the electrodes, i.e. a geometry that provides both the correct cell constant for conductivity of hydrocarbons fluids (typical range 0-100,000 pS/cm), and a sensor whose bulk capacitance (for use in dielectric constant measurement) in the range of measure of readily available low cost commercial IC's (having a typical capacitance measurement span of <10 pF, with a total bulk capacitance at the chip of <20 pF). A sensor with a geometry meeting these requirements is then used to form a very low cost system to accurately determine both conductivity and the dielectric constant of the fluid in question.

The ability to measure both parameters in the same volume of fluid has additional advantages as the measures can be correlated to better determine the "condition" of the hydrocarbon fluid and its ability to remain in service, e.g., lubricating large electrical power and marine diesel engines. The cell conductivity constant for use with hydrocarbon-based oils having a conductivity in the range of 1 to 500,000 pS/M is preferably less than or equal to about 0.1. The cell bulk capacitance of these sensors with hydrocarbon fluids inside results in a bulk capacitance of at least about 4 pF. Additionally, as they are measured on the same volume, they are made at the same temperature. This facilitates the application of thermal corrections to the physical values measured. The electrodes are preferably electrically insulated from a supporting frame by impedances exceeding that of the fluid being measured by several orders of magnitude.

In one embodiment, electronic circuitry is connected to this same geometry sensor with an electronic interface connected to a Microcontroller/Digital signal Processor (DSP). The Microcontroller/DSP both generates synchronous drive signals at various frequencies, while directly digitizing and numerically processing the sensor output. The digitized output is numerically processed in the Microcontroller/DSP into its in-phase and quadrature components from which conductivity and dielectric constant, respectively, are determined. This embodiment results in an even more simplified (lower component count) system. This reduces the required analog signal processing components, and, the complexity they require. The numerical processing of the signals also reduces processing errors typical of analog circuit processors. The Microcontroller DSP can vary 1) the frequency and amplitude of the sensor drive signals, and 2) the duration over which sample signals are processed (to extend the range or resolution of the sensor system). These changes can be then made in real time.

Stated on other words, the Microcontroller has complete control over the process, i.e. it can change the drive frequency to make higher resolution resistive or capacitive measures as needed. If the sensor signal is larger than expected, it can lower the amplitude, in essence thereby extending the range. On the measurement side the Microcontroller/DSP can use an in-phase and phase shifted reference (at the same time to make both measures). It can also choose to integrate the signal over more integer periods of the drive signal period. This reduces the bandwidth of the system, which in turn reduces noise and improves resolution, at the expense of overall sampling. With this much processing run by the Microcontroller/DSP, the sensor can "adapt" in real time to changing physical conditions in the fluid, or, to modify the data quality or quantity that the user may need.

Traditionally capacitance measures are made on dielectrically coated electrodes. This, of course, does not allow the measurement of electrical conductivity, as no current could flow. As the frequency of operation of the system is under Microcontroller/DSP program control, real time altering of the base frequency of operation eliminates the effects of the non coated electrodes, and or to extend the range resolution of the measures. As a result the present invention uses metal electrodes exposed (exposed meaning bare metal or equivalent electrically at least at their opposed, electrically-active surfaces) for both conductivity and dielectric constant measures.

The sensor geometry of this invention is also compatible with other physical measurement property sensors, such as the viscosity sensors manufactured by Vectron International, Teledyne, and Symex. Sensor geometry is meant to include the overall size of the components. For example, the outer diameter and length of the center electrode 7 is similar to an acoustic shear wave viscosity sensor that is commercially available, and therefore the inner electrode 6 could be formed by such a device to provide a third physical measurement (viscosity) of a common volume of fluid.

The invention includes a system and method of operation using the single pair, preferably coaxial, electrode sensor. The system, or device, includes low cost integrated circuits for measuring the conductivity and dielectric constant of a high impedance fluid exposed to the sensor as well as a solid state interface between the sensor and these circuits. The interface bridges differences in the operating electrical parameters of these components, and either automatically switches between the operation of these circuits to produce measurements of conductivity and dielectric constant using only one sensor, or in the second method alters the drive signal and computation path to determine the components. The AC driving signals produced by these circuits are at low frequencies. The combination of a sensor according to the present invention (a single pair of coaxial, exposed metal electrodes defining a cell having the electrical characteristics noted above, and the aforementioned signal processor provides many of the advantages of the invention. In the form of the invention using a Microcontroller/DSP processor to control both drive signals to the sensor, and providing subsequent direct digital conversion with numerical processing of the received sensor signal, results in a sensor electronic system which is especially simple, has low component requirements, and nevertheless meets the resolution requirements for fluid conditioning monitoring.

BRIEF DESCRIPTION OF THE DRAWINGS

FIG. 5A is a cross sectional, FIG. 5B is a frontal, and FIG. 5C is a perspective view of a sensor according to the present invention for the measurement of the conductivity and dielectric constant of a fluid together.

FIG. 6 is a schematic drawing of a front end circuit according to the present invention that interfaces between the sensor shown in FIGS. 1, 3 and 5, to the processor which measures conductivity and dielectric constant of a fluid using the same sensor.

DETAILED DESCRIPTION OF THE INVENTION

Figure 1:
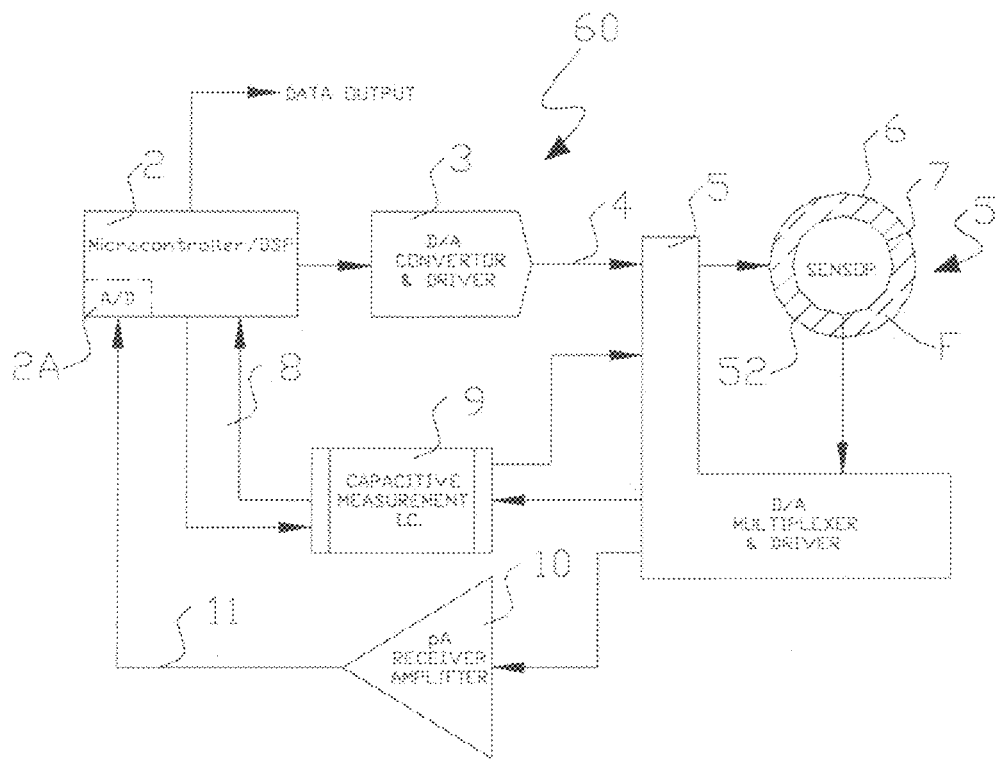
FIG. 1 is a block diagram of the conductivity—dielectric constant measurement components of the sensor system of the present invention.

A sensor 50 according to this invention in the embodiment shown in FIG. 1 has a single pair of coaxial, bare metal electrodes 6, 7 that form a measurement cell 52 that holds a fluid F to be measured. In this exemplary embodiment, the sensor geometries and constants are adapted for a conductivity measurement system for jet fuel & lubricating oils with a range 0-2000 pS/cm (Pico-Siemens/centimeter) with a typical dielectric constant of 2 to 2.5. While the electrodes 6, 7 are preferably all bare metal, it will be understood that what is important is that the fluid F in the measurement cell 52 is in electrical connection with the surface of the electrodes forming that measurement cell 52.

FIG. 1 also shows a multi-parameter measuring system 60 according to this invention having a novel electronic switching interface 5 that allows the combined parameter electrode sensor to interface with the two distinct measurement circuits 10 and 9 for conductivity and dielectric constant, respectively. The interface 5 is designed so that it can handle the very high isolation requirements of measuring conductivity in liquids whose conductivity is <0.1 µS/M, without adding significant capacitance to the circuitry, thereby providing the ability to use an Integrated Circuit (IC) type capacitive measuring device 9, without adding bulk capacitance that exceeds the device 9 measurement range.

The Microcontroller/DSP 2 outputs to the D/A converter and a driver sine wave table such that the signal in line 4 used to drive the sensor 50 is a low frequency high spectral purity sinusoid. Multiplexer 5 connects line 4 to the outer electrode 6 of sensor 50 during conductivity measurement periods. Alternately, multiplexer 5 connects the capacitive measurement IC 9 to the outer electrode 6 of sensor 50 during capacitance (dielectric constant) measurement periods. During conductivity measurement periods the output of the pA receiver amplifier 10 is an AC signal on line 11 proportional to the current flowing in the fluid F. This signal will be compromised of both a resistive in phase component, and the capacitive coupled quadrature component, due to sensor 50 electrodes 6, 7 which form a capacitor. This signal is converted by analog to digital (A/D) converter 2a and numerically processed to determine the in phase component proportional to conductivity by numerical process in Microcontroller/DSP 2. These methods are further described below.

Figure 4:
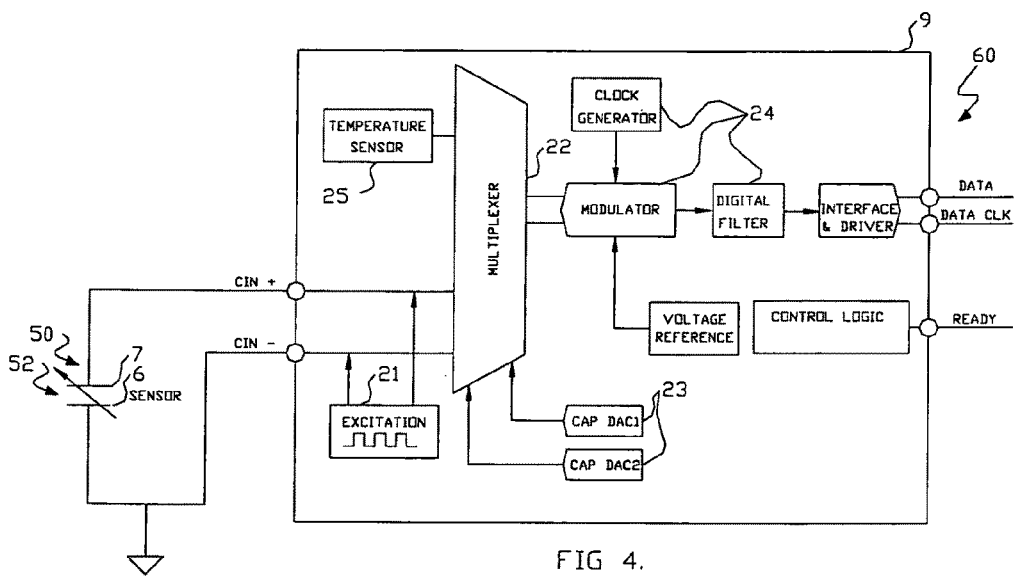
FIG. 4 is a block diagram of an IC for use with the sensor of this invention to produce a dielectric constant measurement of a fluid.

During capacitive measurement periods, IC 9 performs the complete measurement; a block diagram of this IC is detailed in FIG. 4. The determination of capacitance by IC 9 uses the following main components. Excitation module 21 drives a moderate frequency square wave across sensor 50 drive the outside electrode 7. This signal is directed to the modulator detector comprised of items 24 inside the IC via the internal multiplexer 22. Internal control signals of IC 9 are used to determine the amplitude of the signal which is across its inputs at CIN+_ and CIN−. Additionally, offsetting DAC1 and DAC2 23 can be used to reduce the bulk capacitance that sensor 50 presents to IC 9.

Temperature measurement is an essential component as all conductivity measurement should be referenced to a known temperature due to the temperature dependence of conductance. IC 9 has built-in temperature sensor 25 which is interfaced to the same measurement circuit 24 through an internal (IC) multiplexer 22.

The sensor 50 is physically designed so that its own bulk capacitance is compatible with the IC operating circuit, e.g. as show in detail in FIG. 4, having typical input ranges of +/−8 pF, and bulk capacitance offsetting ability less than 20 pF (the user can set the offset by a set amount). The sensor 50 has two coaxial, metallic electrodes; the inner electrode 7, shown with a preferred cylindrical outer surface, and the outer electrode 6 with a mutually spaced inner cylindrical surface that together define a measurement cell 52 of the sensor 50. Electrode 7 is also of a geometry to enable the mounting of Vectron, Teledyne or other manufacturer viscosity sensor, to provide the ability to add a measure of this physical parameter of the fluid, to further understand the condition of the fluid. The sensor 50 is preferably of the same general type as the prior art two coaxial electrode, AC actuated, JF 1A sensor 50' shown in FIG. 2 and manufactured and sold by D-2, Inc. for monitoring flowing aviation fuel (like parts in the various embodiments are denoted with the same reference number, but distinguished with a prime.). The sensor 50' is formed by outer electrode 16 (shown displaced axially for clarity), inner electrode 15, high impedance isolator 14, sensor housing 13 and sensor stem 121. The sensor 50 of the present invention is modified from this prior art sensor according to the present invention, as detailed below, and elsewhere herein.

For conductivity measurement the sensor 50 is constructed so that it has:
Cell Constant of about 0.1 or lower
Range: 1 pS/M as the least detectable to 2,000 pS/CM
Resolution: 16 bit (1 part in 65036)
Frequency of Operation: <1 KHz, typically less than 100 Hz, and preferably less than 10 Hz
Sample Rate: 0.5 Hertz
Power: <30 mW For dielectric constant measurement, sensor 25 is constructed so that it has:
Cell Bulk Capacitance: about >4 pF (with hydrocarbon fluid in cell)
Range: 1-3 Dielectric Constant
Range: Least Detectable Change of about 100 fF (femto Farad)
Range Transfer: Least Detectable H2O in oil is typically 20 ppm
Range Transfer: Least Detectable H2O in oil for a worst case is 100 ppm
Frequency of Operation: <20 KHz, and preferably <3 KHz
Sample Rate: 0.5 Hertz
Power: <30 mW For measurement of electrical conductivity of a fluid, AC measurement of conductivity overcomes the problems associated with polarization impedance due to the DC Polarization effect, that is, a steady decline in the ability of the sensor to conduct charges across the electrodes with a DC field applied after an initial spike to a high value. The decline appears as the charge builds on each of the electrodes. Ultimately the flow of charge stops, indicative of an infinite impedance.

By rotating the electric field (AC Measurement), the establishment of charges on each electrode does not occur, and a true measure of the current flowing can be made. The measure is independent of the "polarization" of the electrodes. AC measurement approach eliminates the polarization effect, which facilitates the measurement of the conductivity of flowing fluids with extremely low conductivity. The measure also then becomes flow rate through the sensor insensitive.

Figure 3:
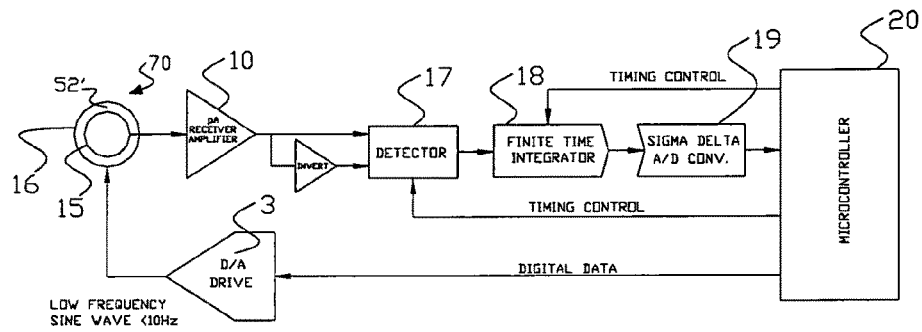
FIG. 3 is a block diagram of the prior art AC analog drive signal generation and measurement circuitry used with in the prior art aviation fuel sensor shown in FIG. 2.

FIG. 3 is a block diagram of the basic elements of the prior art conductivity measurement approach. A microcontroller 20 generates a low frequency sine wave digitally by outputting sine table data values successively to the D/A drive 3. The drive 3 ensures that the sinusoidal drive signal is symmetrical around zero and is not affected by the load of the sensor formed by electrodes 15,16. The drive 3 removes any higher frequency small steps due the discrete values output by the D/A. The drive 3 is connected directly to the outer electrode 16 of the sensor. The outer electrode 16 is isolated from the inner electrode 15 by an isolator 14. The isolator 14 is fabricated from a high dielectric strength material, for example, PolyEthylEthylKetone (PEEK). (The sensor 50 of the present invention uses a like isolator.) The hydrocarbon fluid under test provides a resistive (in-phase with the drive signal) conduction path from the outer electrode 16 to the inner electrode 15. The impedance of the conductivity measurement across coaxial electrodes 15 and 16, when immersed in hydrocarbons electrodes, is typically >3000×$10^6$ ohms where the conductances of the hydrocarbon fluids are in the 0-2,000 pS/M range. The electrodes 15, 16 also form a capacitor, so a capacitive coupled current (90 degrees shifted from the drive signal, termed the quadrature signal) also flows that, in the prior art, is an error signal. To reduce the effect of the quadrature signal, a low drive frequency (typical less than 10 Hz) is used so that the quadrature component of the received signal is small compared with the in-phase signal. Additionally, the prior art received signal processor is specifically designed only to respond to the in-phase signal. This is further described below.

The sensor current is amplified by a high performance pico-amp current amplifier 10. The amplified signal is detected at detector 17 by multiplication with a reference square wave that is in-phase with the drive signal. The output of the detector 17 is then integrated over integer periods of the of the drive frequency by the finite time integrator 18. At the end of each finite time integration, the microcontroller 20 converts the DC voltage output of integrator 18 using a high resolution A/D convertor 19. Values from the A/D converter 19 are further scaled into physical units using the physical scale factor of the sensor and provided to the user. This synchronous detection and finite time integration further reduces the sensitivity of the prior art sensor system to the quadrature voltage effects.

The same FIG. 3 circuitry can also be used to measure dielectric constant (capacitance) across the electrodes by substituting a quadrature reference into the detector 17. A quadrature reference is a signal which is 90 degrees out of phase from the drive signal. As a result the circuit responds to the capacitive coupled signal across the electrodes, which will be in quadrature with the reference signal, whereas, the resistively detected signal is in-phase with the reference signal. The circuitry then responds to the change in capacitance across the electrodes. The capacitance across the electrodes is the product of the physical size of the electrodes, which is fixed, and the dielectric constant of the material between them.

Figure 2:
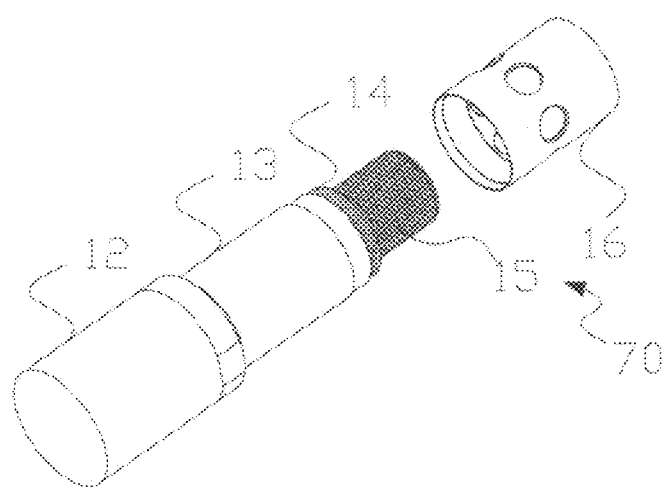
FIG. 2 is a view in perspective of a prior art aviation fuel sensor using a coaxial electrode pair to measure only conductivity, with the outer electrode shown as displaced axially.

A known industrial conductivity sensor shown in FIG. 2 is manufactured and sold by D-2, Inc. under Model No. JF-1A.

A key characteristic of such a coaxial sensor, and of the sensor 50 of the present invention, is its cell constants (volume measured constants), explained below, for both the conductivity constant (cell factor) and dielectric cell constant.

Conductivity is a "volume" measure that units are pS/M (area $M^2$/Length M)

Cell Factor is a "volume" correlation factor for the sensor geometry.

$$R = 1/C$$

$$1/c = r = k1/c$$

Where:
R=Resistivity in ohms/M
C=Conductivity in S/M
c=Conductance in Siemens
r=Resistance in Ohms
k=Cell Factor The dielectric constant of the cell is defined as detailed below.

Dielectric Constant is the ability of a material to hold an electric field constant; dielectrics are polarized by an electric field.

The Ratio of the field in a vacuum to the field in the dielectric is defined as the Dielectric Constant:

$$Ed = Eo/1+_x = Eo/k$$

where:
Ed=Field within the dielectric
Eo=Applied electric field
X=Electric susceptibility of the material
K=Dielectric Constant Dielectric Constant is most frequently measured by means of capacitance Electric Field on a capacitor in a vacuum $$Vv = Q/A\bar{e}d$$

where:
Q=Charge applied to one plate
Vv=Potential difference between the plates
A=Area of the plates
$\bar{e}$=Permittivity constant
d=Plate Separation Electric field on a capacitor with a dielectric $$Vv = Q/kA\bar{e}d$$

where:
K=dielectric constant

Capacitance is defined as:

$$C = Q/V$$

Substituting into the previous equations $$Cv = A\bar{e}/d (\text{Vacuum}) \quad Cd = kAe/d (\text{Dielectric})$$

So if one measures the Value of Capacitance in air and then with the unknown dielectric (fluid) for a fixed geometry of electrode plates, the dielectric constant for the material can be determined by:

$$K = Cd/Cv$$

Since Dielectric Constant K is simply a ratio, it has no units.

Some representative D.C.'s are given in the following table.

| Substance | Dielectric Constant |
|---|---|
| Vacuum | 1.0000 |
| Air | 1.006 |
| Lubricating Oil | 2.2 |
| Alcohol | 38 |
| Water | 81 |

FIG. 4 shows a block diagram of circuitry 9, a comparatively low cost commercial IC, used in the present invention for the measurement of dielectric constant using the coaxial two electrode sensor 50 of this invention. This block diagram is representative of several commercial integrated circuits developed by various companies that place this circuitry on a single IC. The benefit of these single IC's is they perform the complete function in a single integrated circuit. As noted above, these sensor chips were primarily designed for touch panel detection. While they are cost effective, a limitation of these commercial chips is their limited total capacitance range, including the maximum value of bulk capacitance which they can subtract from the applied input.

Typical ranges for commercial chips of this type are ranges of +/−10 pF, across a bulk capacitance of up to about 20 pF.

The AD 7747 chip manufactured by Analog Devices is an example of such an IC 9. It is a 24-bit capacitance to digital converter and includes a temperature sensor.

Standard commercial capacitance sensor chip size of the type shown in FIG. 4 can have a very small size, e.g. with a chip body about 4.4 mm side, 5.0 mm long and 0.15 mm thick, exclusive of dual-in-line connector pins.

The bulk capacitance for a coaxial sensor such as the sensor 50. can be found from:

The capacitance of a coaxial structure can be computer by:

$$C = 2 * \pi * \bar{e} * L / ln(a/b)$$

where:
L=Length
a=I.D. of outer electrode
a=O.D. of inner electrode
$\bar{e}$=Permittivity Constant The measurement of absorbed and/or condensed water in lubricants is of particular interest in monitoring the condition of the lubricant. The present invention can provide a measurement of this important, and heretofore difficult to measure parameter, particularly where the measurement is in line to monitor a flowing fluid in real time, e.g. the flow of a lubricant in a "rifle" manifold within an internal combustion engine block feeding pumped lubricant to valves and the like.

The following discussion explains why this is a difficult problem, and the usefulness of this invention in being able to measure it.

Capacitance is directly proportional to the dielectric constant of the material between the plates.

One would expect that if a given volume, say 0.1% (1000 ppm) of oil with D.C.=2.2 is replaced with water D.C.=80, the change in capacitance would be given by the equation $$\Delta C = 1 - (2.2*0.001 + 80*0.999)/2.2 = 35,000 \text{ ppm}$$

However, free (non-absorbed) water in the lubricant tends to form as very small, generally spherical, droplets suspended in the surrounding oil "matrix." These drops tend to couple electrically in series with one another, which skews the usual volume model for electrical measurements given above. A model for the effect of the suspended droplets is provided in "Electrical Properties of a Dielectric Matrix with Spherical Inclusions of Metal (Conductors)" of: A. F. Chudnovski and L. V. Gorfunkel, Agrophysical Scientific Research Institute, Leningrad, the disclosure of which is incorporated herein by reference.

Result is for aqueous salt dispersed in oil:

$$Eav/Eo=1+\theta/1-2\theta$$

where:
Eav=Average electric field
Eo=Electric field in vacuum
$\theta$=Concentration Applying the Chudnovski et al. theoretical "spherical inclusions" model to the 1000 ppm water example:

$$\Delta C=1-1+0.001/1-2*0.001$$

$$\Delta C=0.0036=3000 \text{ ppm}/1000 \text{ ppm water}$$

This is a factor of 10 sensitivity lower than the volume computation gives.

This theoretical result (factor of 10 reduced sensitivity) has also been confirmed experimentally by the Applicant.

The theoretical equations work for water concentrations below those that result in the sphere of water fully shorting together, around a concentration of 0-0.3.

Despite this loss of sensitivity in changes of Dielectric Constant (D.C.) in lubrication oil, aviation fuel, or hydraulic fluid due to contamination by a higher dielectric species such as water or drill mud, the measurement system 50, 60 of this invention has adequate sensitivity to detect the change. The present invention can detect ~100 femto farad changes, which correspond to ~30-50 ppm water content change. In similar manner the detection of drill mud which has a dielectric constant similar to water in hydraulic fluid faces similar sensitivity issues hence the requirement of precise capacitance measures to provide a meaningful commercial detection level. Drill mud is considered a contaminating source in a hydraulic fluid system.

The foregoing sets the "minimum" sensitivity for the combined conductivity dielectric constant measurement of the present invention in terms of its capacitance sensitivity. It also sets the limits of the variability of capacitance that the common set of electrodes 6, 7, and switching circuitry 5 (FIG. 1) can attribute to the measurement without effecting the measurement of the capacitance of interest—the change in capacitance of the fluid in the sensor.

The geometry of the sensor 50 of the present invention provides in a two electrode, coaxial sensor suitable to both measurements, in other words, the coaxial sensor has all of the following: correct K constant for conductivity (<0.1), a minimum bulk capacitance (<20 pF) that can be handled by "commercially available" integrated circuits, electrodes which have electrical isolation from each other at least 100-1000 times the highest impedance of the fluid ($>1\times10^{15}$ ohms). In addition, the electronics 5 (FIG. 1) that switch from the conductance circuitry to the capacitance measurement circuitry does not affect the measures to be made. The present invention combines a single coaxial electrode sensor with discrete measurement electronics to form a multi-parameter fluid condition sensor.

By way of illustration but not of limitation, the current preferred embodiment of the sensor 50 has an outer electrode 6 with inner diameter of 1 inch and inner electrode 7 with outer diameter of 0.9 inch mounted into a ½ inch national pipe thread (NPT) holder. This results in a sensor 50 with K=0.05, and, a bulk capacitance of 4 pF when filled with hydrocarbon fluid F (nominal dielectric constant of 2.0).

The implementation of the invention the two electrode, coaxial geometry for sensor 50 shown in FIG. 5. is preferred, although other geometrical configurations of the electrodes could also be applied, as example, flat plate, three electrodes, etc. The coaxial geometry, as one example of its advantages, allows both the inner and outer electrodes to expand and contract together in response to changes in temperature, thereby providing a more stable sensor.

In order to switch between the two measurement circuits (conductivity and dielectric constant (capacitance)), one embodiment of the invention preferably includes a solid state electronic interface 5' shown in FIG. 6 using switches S1, S2, S3, or relays, or optocouplers, connected between inputs from the sensor electrodes 6, 7 and the circuits 10, and 9 as also shown in FIG. 6. The switches S1, S2, S3 can be the solid state relay Model PS7802 manufactured by California Eastern Laboratory or the Hewlett Packard HPCL 4701. The Aligent HP070A "electronic solenoid" and other similar devices can also serve as the interface switches.

The electronic switch performance is nearly equal to what can be obtained in a traditional air gap solenoid switch in terms of the on/off impedance ratio of the device, $>1\times10^9$. The switch device does not add significant bulk capacitance to the input of the commercial capacitance measurement IC 9. The optical couplers (solid state relays) meet these requirements with open circuit bulk capacitance of <10 pF. Additionally the switch bulk capacitance is stable with ambient temperature or changes in it; otherwise the switch bulk capacitance changes could be distinguished from changes in the measured fluid. For a fluid condition sensor, specifically lubricating oil, operation is expected over the range of −40 to +125 C. Resistor R5 in series with drive 3 eliminates the need for a fourth switch, as the Microcontroller/DSP 2 can stop the D/A output changes during capacitive measurement periods. R5 then provides a reasonably high impedance path to ground for the capacitive measurement IC 9 output drive signal. Hence, the front end design of a circuit as shown in FIG. 6 minimizes the number of switch elements. This lowers the cost and complexity of the front end circuitry and the sensor system overall.

This measurement system of this invention combines AC conductivity measurement, commercial IC's for the measure of fluid capacitance, and working in combination with a single pair electrode multiple parameter sensor capable of measuring the key physical properties of fluid condition in high impedance hydrocarbon fluids, including oil with admixed water droplets and other contaminants such as drill mud.

Figure 7:
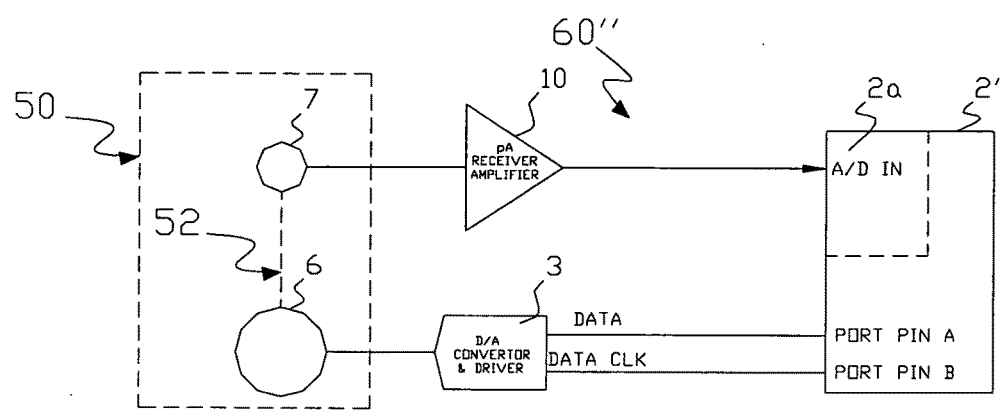
FIG. 7 is a block diagram of front end circuit that interfaces between the sensor and DSP processor in which the DSP processor performs the computation of conductivity and dielectric constant, where the source signal is modified by the DSP, and the computation performs isolation of the in-phase and quadrature components of the received signal.

In a further, simplified, alternative embodiment of the present invention shown in FIG. 7, the discrete multiplexer 5 and capacitive measuring IC 9 shown in the FIG. 6 embodiment are omitted. The amplifier 10 output is directly digitized by the analog to digital (A/D) converter 2a in the Microcontroller/DSP 2'.

In this embodiment the same D/A Driver circuit 3 drives a signal onto the outer electrode 6. Conductivity is measured as previously described using a low frequency sine wave, while, capacitance is measured using either a higher frequency sine wave or square wave, with the choice based on the range and resolution required by the system in order to attain meaningful physical measures. The increased frequency provides higher resolution by reduction in impedance across the sensor electrodes 7. The same amplifier 10 as previous described is used to amplify the signal from the inner electrode 7.

An internal ND converter 2a of the microcontroller/DSP 2' has a typical resolution of 12 bits. Its resolution is not critical to the overall resolution of the system. The input signal is digitized by the Microcontroller/DSP 2' at a sampling rate several order of magnitude above the drive signal Nyquist frequency.

The Microcontroller/DSP multiplies the input ND values times the reference signal of interest. Conductivity is determined by the multiplication of the input D/A values times the in-phase reference, and correspondingly capacitance (Dielectric Constant) values are multiplied time the quadrature reference. The output of the multiplicands are integrated (summed) over integer number of the of the drive signal period. These values are then scaled and reported to the user via the Microcontroller/DSP 2' serial interface. Final resolution/noise/accuracy of the system is then related only to the accuracy of the drive signal, the AC gain stability of the receiver amplifier, and the number of cycles over which the base signal is processed and integrated over in the Microcontroller/DSP.

By way of illustration, but not of limitation, in a suitable microprocessor, or microprocessor with integrated DSP 2', is manufactured by Micro-chip as its Ex DSPIC30F series.

As this embodiment eliminates IC 9 along with its temperature sensor 25, a secondary circuit must be provided to measure temperature. Low cost IC temperature IC's with direct voltage output can be used to replace the IC 9 temperature function, as example LTC1047 manufactured by Microchip Technologies, Incorporated.

While the invention has been described with respect to the foregoing embodiments, it will be understood that various modifications and variations will be made by those skilled in the art. Such modifications and variations are intended to fall within the scope of the following claims.

What is claimed is:

1. A device for the direct measurement of plural parameters of a hydrocarbon based fluid comprising:
   a sensor comprising a single pair of mutually spaced coaxial electrodes that define a measurement cell that can receive said fluid and be in direct electrical connection with said fluid in said cell, said cell being configured and sized to have a conductivity cell factor of about 0.1 or less and a bulk capacitance of at least 4 pF with said hydrocarbon fluid in said cell;
   an integrated circuit electrically connected to said sensor to measure the conductivity for said fluid with an AC excitation drive signal;
   an integrated circuit electrically connected to said sensor to measure the dielectric constant of said fluid with an AC excitation drive signal; and
   an interface electrically connected between said sensor and both said conductivity and dielectric constant integrated circuits, said interface circuit matching the electronic characteristics of at least said sensor and said dielectric constant integrated circuit, wherein said interface comprises solid state relay switches being optocouplers that multiplex said sensor as an input to both said conductivity and said dielectric constant integrated circuits.

2. The device of claim 1 further comprising a temperature sensor that measures the temperature of the sensor and a temperature compensation circuit that automatically corrects the measurements produced by said conductivity and dielectric constant integrated circuits for variations in temperature.

3. A method for directly measuring multiple parameters of a hydrocarbon based fluid comprising:
   placing the fluid between a single pair of opposed, mutually spaced coaxial electrodes of a sensor, the electrodes defining a measurement cell that can receive said fluid and be in direct electrical connection with said fluid in said cell;
   configuring and sizing the sensor to have a conductivity cell factor of about 0.1 or less and a bulk capacitance of at least 4 pF with said hydrocarbon fluid in said cell so that AC excitation of the sensor provides inputs for measurement of at least two of said multiple parameters, the conductivity and the dielectric constant of the fluid, using integrated circuits for said conductivity and dielectric constant measurements; and
   providing an interface electrically connected between said sensor and both said conductivity and dielectric constant integrated circuits that matches the electrical characteristics of said sensor to those required by said conductivity and dielectric constant integrated circuits, wherein said interface comprises solid state relay switches being optocouplers that multiplex said sensor as an input to both said conductivity and said dielectric constant integrated circuits.

4. The measurement method of claim 3 wherein said electrodes include bare metal surfaces that are in contact with said fluid.

5. The measurement method of claim 3 wherein said measurements of said multiple parameters are simultaneous, using the inphase and quadrature variance of the drive signal with respect to a detector reference signal to measure the conductivity and dielectric constant, respectively, of the fluid.

6. The measurement method of claim 4 wherein said measurement varies the frequency of the AC drive signals as a function of the parameter being measured.

7. The measurement method of claim 4 wherein said measurement varies the amplitude of the drive signal.

* * * * *